(12) United States Patent
Rajguru et al.

(10) Patent No.: US 12,419,607 B2
(45) Date of Patent: Sep. 23, 2025

(54) INTRALUMINAL IMAGING FOR REFERENCE IMAGE FRAME AND TARGET IMAGE FRAME CONFIRMATION WITH DEEP BREATHING

(71) Applicant: PHILIPS IMAGE GUIDED THERAPY CORPORATION, San Diego, CA (US)

(72) Inventors: Nikhil Sreedhar Rajguru, San Diego, CA (US); Harold Agnes Wilhelmus Schmeitz, Eindhoven (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 216 days.

(21) Appl. No.: 18/083,080

(22) Filed: Dec. 16, 2022

(65) Prior Publication Data

US 2023/0190226 A1    Jun. 22, 2023

Related U.S. Application Data

(60) Provisional application No. 63/292,510, filed on Dec. 22, 2021.

(51) Int. Cl.
*A61B 8/08*         (2006.01)
*A61B 8/00*         (2006.01)
(Continued)

(52) U.S. Cl.
CPC ............. *A61B 8/0891* (2013.01); *A61B 8/12* (2013.01); *A61B 8/461* (2013.01); *A61B 8/5223* (2013.01);
(Continued)

(58) Field of Classification Search
CPC ........... A61M 16/04–0497; A61M 2039/0279; A61M 2039/0626; A61B 8/0891;
(Continued)

(56) References Cited

U.S. PATENT DOCUMENTS 6,200,268 B1   3/2001   Vince
6,381,350 B1   4/2002   Klingensmith
(Continued)

*Primary Examiner* — Sean A Frith

(57) ABSTRACT

A system includes a processor circuit that receives intraluminal images obtained by an intraluminal imaging device during movement through a patient's body lumen. The processor circuit outputs, to a display, a visual representation of user guidance in response to the processor circuit identifying, among the intraluminal images, a candidate intraluminal image. The user guidance includes stopping the movement and instructing the patient to initiate deep breathing. The processor circuit receives additional intraluminal images obtained by the intraluminal imaging device while the movement is stopped and the patient is deep breathing. The processor circuit determines if a shape and/or size of the body lumen changes in the additional intraluminal images. The processor circuit accepts or rejects the candidate intraluminal image based on if the shape and/or size of the body lumen changes. The processor circuit outputs, to the display, a visual representation corresponding to accepting or rejecting the candidate intraluminal image.

14 Claims, 12 Drawing Sheets

(51) Int. Cl.
*A61B 8/12* (2006.01)
*G06T 7/00* (2017.01)

(52) U.S. Cl.
CPC .. *G06T 7/0014* (2013.01); *G06T 2207/10132* (2013.01); *G06T 2207/30101* (2013.01)

(58) Field of Classification Search
CPC ......... A61B 8/12; A61B 8/461; A61B 8/5223; A61B 8/54; A61B 1/00002–000094; G06T 7/0014; G06T 2207/10132; G06T 2207/30101
See application file for complete search history.

(56) References Cited

U.S. PATENT DOCUMENTS

| | | | |
|---|---|---|---|
| 6,776,763 B2 | 8/2004 | Nix | |
| 7,074,188 B2 | 7/2006 | Nair | |
| 7,175,597 B2 | 2/2007 | Vince | |
| 7,215,802 B2 | 5/2007 | Klingensmith | |
| 7,226,417 B1 | 6/2007 | Eberle | |
| 7,359,554 B2 | 4/2008 | Klingensmith | |
| 7,463,759 B2 | 12/2008 | Klingensmith | |
| 7,846,101 B2 | 12/2010 | Eberle | |
| 7,930,014 B2 | 4/2011 | Huennekens | |
| 8,290,228 B2 | 10/2012 | Cohen | |
| 8,463,007 B2 | 6/2013 | Steinberg | |
| 8,670,603 B2 | 3/2014 | Tolkowsky | |
| 8,693,756 B2 | 4/2014 | Tolkowsky | |
| 2007/0293760 A1* | 12/2007 | Schaafsma | A61B 5/4884 600/454 |
| 2009/0270850 A1* | 10/2009 | Zhou | A61B 18/24 600/459 |
| 2012/0179042 A1* | 7/2012 | Fukumoto | A61B 8/0891 600/443 |
| 2013/0216114 A1* | 8/2013 | Courtney | A61B 5/33 382/128 |
| 2015/0339847 A1* | 11/2015 | Benishti | A61B 5/026 382/131 |
| 2018/0085170 A1 | 3/2018 | Gopinath | |
| 2019/0261957 A1* | 8/2019 | Zaslavsky | A61B 8/565 |
| 2019/0282182 A1 | 9/2019 | Scott | |
| 2020/0129142 A1* | 4/2020 | Chao | A61B 8/5223 |
| 2020/0129147 A1 | 4/2020 | Nair | |
| 2020/0390345 A1* | 12/2020 | Haase | A61B 34/10 |
| 2022/0338833 A1* | 10/2022 | Dhatt | A61B 8/5207 |

\* cited by examiner

INTRALUMINAL IMAGING FOR REFERENCE IMAGE FRAME AND TARGET IMAGE FRAME CONFIRMATION WITH DEEP BREATHING

TECHNICAL FIELD

The present disclosure relates generally to identifying and treating regions of vessel constriction in blood vessels, such as peripheral veins. In particular, intraluminal images are acquired while an intraluminal imaging device is stationary and while the patient breathes deeply to confirm accurate selection of reference frames associated with healthy regions of a vessel and target frames associated with constricted regions of a vessel.

BACKGROUND

Intraluminal imaging is used in interventional treatment of peripheral vasculature as a diagnostic tool for assessing a diseased vessel, such as a peripheral vein, within the human body to determine the need for treatment, to guide the intervention, or to assess its effectiveness. An intraluminal imaging device including one or more ultrasound transducers is passed into the vessel and guided to the area to be imaged. The transducers emit ultrasonic energy. Ultrasonic waves are partially reflected by discontinuities in tissue structures (such as various layers of the vessel wall), red blood cells, and other features of interest. Echoes from the reflected waves are received by the transducer and passed along to an intraluminal imaging system. The imaging system processes the received ultrasound echoes to produce a cross-sectional image of the vessel where the device is placed.

A peripheral vein, such as the renal or femoral vein, may become constricted by an obstructive tissue such as a blood clot or webbing within the vein, wall injury by long term trauma from contact with neighboring structures, or by compression by a structure external to the vein. This constriction can lead to reduced blood flow and symptoms like swelling, soreness, or pain to name a few. To remedy this root cause, a physician must identify the region of constriction along the vein and select a proper solution, such as placing a stent.

A physician may use an intraluminal imaging device to determine the location and extent of a constriction of a vessel. This information may inform the type of treatment device selected as well as the location at which the device is deployed. However, as a patient breathes during an imaging procedure, the patient's veins contract and expand with the inhalations and exhalations respectively. An image yielded during contraction of veins within the patient's body may make accurate interpretation of a vein more prone to error and can lead to incorrectly determining the location or severity of a constriction and selecting incorrect treatment. For example, an incorrectly sized stent may lead to the eventual dislocation of the stent or rupturing of the treated vein. A stent may also be placed where no stent is needed.

SUMMARY

Embodiments of the present disclosure are systems, devices, and methods for confirming correct identification of candidate reference frames and candidate compression frames during an intraluminal imaging procedure. In particular, as an intraluminal imaging catheter images a patient's vein, the system identifies a location of a potential candidate reference frame. The system then instructs the physician to stop moving the catheter and instructs the patient to breathe deeply. As the patient inhales, the patient's veins contract. As the patient exhales, the veins expand. If the imaged vein changes in shape and size greater than a threshold amount, the system confirms that the location of the catheter corresponds to a candidate reference frame and the image frame with the greatest vein size in the breathing cycle is selected as the candidate reference frame. This location is a healthy region of the vein.

At a constricted region of the vein, the system identifies a location of a potential candidate target frame. The system, again, instructs the physician to stop moving the catheter and the patient to start breathing deeply. If there is little or no change to the shape and size of the vein at this location, the system confirms the candidate target frame and the intraluminal image frame showing the greatest vein size in the breathing cycle is selected as the candidate target frame. This location is a constricted region of the vein.

Embodiments of the present disclosure advantageously assist physicians in identifying healthy and constricted regions of a vein by ensuring an identified reference frame is correctly classified as a reference frame and an identified target frame is correctly classified as a target frame. In addition, it advantageously assists physicians to make accurate measurements by selecting the frame of largest cross-sectional area. With accurate measurements, the proper treatment can be selected, such as the correct size or location of a stent.

In an exemplary aspect of the present disclosure, a system is provided. The system includes a processor circuit configured for communication with an intraluminal imaging device and a display, wherein the processor circuit is configured to: receive a first plurality of intraluminal images obtained by the intraluminal imaging device during movement of the intraluminal imaging device through a body lumen of a patient; output, to the display, a visual representation of first user guidance in response the processor circuit identifying, among the first plurality of intraluminal images, a candidate intraluminal image, wherein the first user guidance comprises stopping the movement of the intraluminal imaging device and instructing the patient to initiate deep breathing; receive a second plurality of intraluminal images obtained by the intraluminal imaging device while the movement of the intraluminal imaging device is stopped and the patient is deep breathing; determine if at least one of a shape or a size of the body lumen changes in the second plurality of intraluminal images; accept or reject the candidate intraluminal image based on if at least one of the shape or the size of the body lumen changes; and output, to the display, a visual representation corresponding to accepting or rejecting the candidate intraluminal image.

In some aspects, the processor circuit is configured to reject the candidate intraluminal image as a reference intraluminal image in response to at least one of the shape or the size of the body lumen not changing. In some aspects, the processor circuit is configured to accept the candidate intraluminal image as a reference intraluminal image in response to at least one of the shape or the size of the body lumen changing. In some aspects, the processor circuit is configured to select, from the second plurality of intraluminal images, an intraluminal image with a largest lumen as the reference intraluminal image. In some aspects, the processor circuit is configured to output, to the display, a visual representation of second user guidance, wherein the second user guidance comprises resuming the movement of the intraluminal imaging device and instructing the patient to stop deep breathing. In some aspects, the processor circuit is configured to reject the candidate intraluminal image as a target intraluminal image in response to at least one of the shape or the size of the body lumen changing. In some aspects, the processor circuit is configured to accept the candidate intraluminal image as a target intraluminal image in response to at least one of the shape or the size of the body lumen not changing. In some aspects, the processor circuit is configured to select, from the second plurality of intraluminal images, an intraluminal image with a largest lumen as the target intraluminal image. In some aspects, the processor circuit is configured to output, to the display, a visual representation of second user guidance, wherein the second user guidance comprises resuming the movement of the intraluminal imaging device and instructing the patient to stop deep breathing. In some aspects, the processor circuit is configured to determine if the movement of the intraluminal imaging device is stopped. In some aspects, the processor circuit is configured to determine the second plurality of intraluminal images comprises a complete deep breathing cycle. In some aspects, the processor circuit is configured to determine if at least one of the shape or the size of the body lumen changes based on an aspect ratio of the body lumen in the second plurality of intraluminal images. In some aspects, the body lumen comprises a peripheral vein. In some aspects, the system further comprises the intraluminal imaging device.

In an exemplary aspect of the present disclosure, a system is provided. The system includes: an intravascular ultrasound (IVUS) imaging catheter; a processor circuit configured for communication with the IVUS imaging catheter and a display, wherein the processor circuit is configured to: receive a first plurality of IVUS images obtained by the IVUS imaging catheter during movement of the IVUS imaging catheter through a peripheral vein of a patient; output, to the display, a visual representation of user guidance in response the processor circuit identifying, among the first plurality of IVUS images, a candidate IVUS image, wherein the user guidance comprises stopping the movement of the IVUS imaging catheter and instructing the patient to initiate deep breathing; receive a second plurality of IVUS images obtained by the IVUS imaging catheter while the movement of the IVUS imaging catheter is stopped and the patient is deep breathing; determine if at least one of a shape or a size of the peripheral vein changes in the second plurality of IVUS images; accept or reject the candidate intraluminal image as a reference IVUS image or a target IVUS image based on if at least one of the shape or the size of the peripheral vein changes; and output, to the display, a visual representation corresponding to accepting or rejecting the candidate IVUS image.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
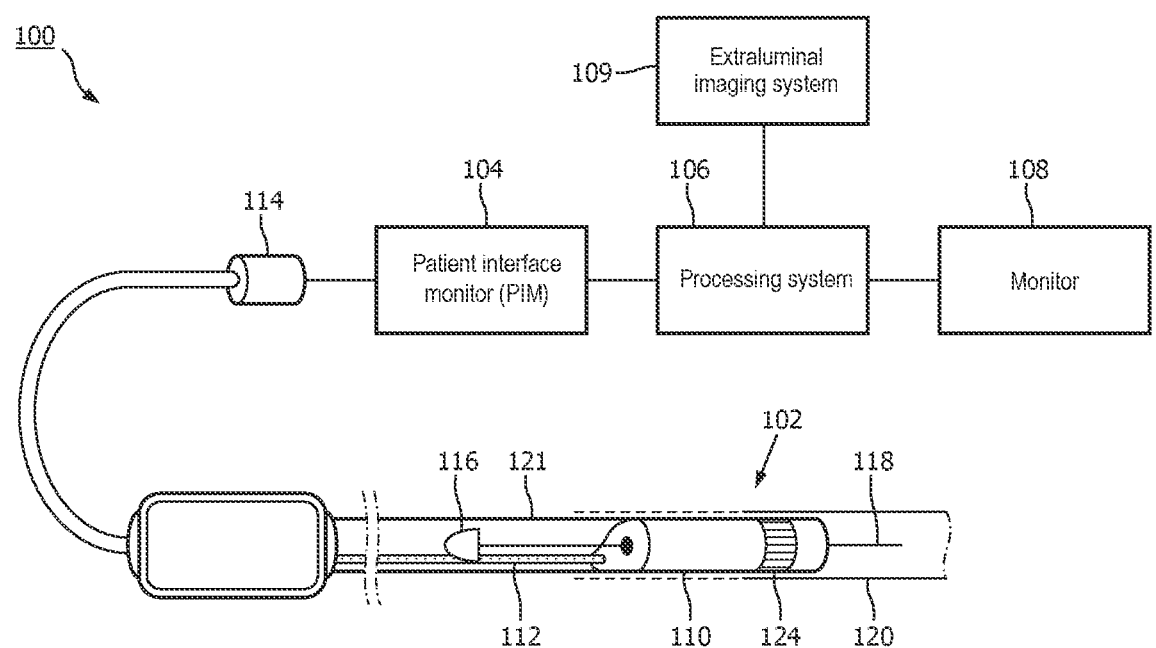
FIG. 1 is a schematic diagram of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100, according to aspects of the present disclosure. The intraluminal imaging system 100 can be an ultrasound imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be an IVUS imaging device, such as a solid-state IVUS device.

At a high level, the IVUS device 102 emits ultrasonic energy from a transducer array 124 included in the scanner assembly 110, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the processing system, console, or computer 106 where the ultrasound image (including flow information in some embodiments) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on integrated circuit controller chip(s) of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. The vessel 120 may represent fluid filled or surrounded structures, both natural and man-made. The vessel 120 may be within a body of a patient. The vessel 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to solid-state IVUS catheters, such as the EagleEye® catheter and the Visions® PV.035 catheter available from Koninklijke Philips N. V., and/or those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In some embodiments, the intraluminal imaging device 102 may acquire intravascular images of any suitable imaging modality, including optical coherence tomography (OCT), intravascular photoacoustic (IVPA), intracardiac echocardiography (ICE), and/or other imaging modality.

In some embodiments, the intraluminal device 102 is a pressure sensing device (e.g., pressure-sensing guidewire) that obtains intraluminal (e.g., intravascular) pressure data, and the system 100 is an intravascular pressure sensing system that determines pressure ratios based on the pressure data, such as fractional flow reserve (FFR), instantaneous wave-free ratio (iFR), and/or other suitable ratio between distal pressure and proximal/aortic pressure (Pd/Pa). In some embodiments, the intraluminal device 102 is a flow sensing device (e.g., flow-sensing guidewire) that obtains intraluminal (e.g., intravascular) flow data, and the intraluminal system 101 is an intravascular flow sensing system that determines flow-related values based on the pressure data, such as coronary flow reserve (CFR), flow velocity, flow volume, etc.

In some embodiments, the processing system 106 may also be in communication with an extraluminal imaging system 109. In some embodiments, the system 100 may be described as an intraluminal imaging and extraluminal imaging system 100 and may include two separate systems or be a combination of two systems: an intraluminal sensing system and an extraluminal imaging system. The intraluminal sensing system obtains medical data about a patient's body while the intraluminal device 102 is positioned inside the patient's body. For example, the intraluminal sensing system can control the intraluminal device 102 to obtain intraluminal images of the inside of the patient's body while the intraluminal device 102 is inside the patient's body as described previously. The extraluminal imaging system 109 obtains medical data about the patient's body while an extraluminal imaging device is positioned outside the patient's body. For example, the extraluminal imaging system 109 can control the extraluminal imaging device to obtain extraluminal images of the inside of the patient's body while the extraluminal imaging device is outside the patient's body.

The processing system 106 may be in communication with the extraluminal imaging system 109 through any suitable means or components. Such communication may be established through a wired cable, through a wireless signal, or by any other means. In addition, the imaging system 100 may be in continuous communication with the extraluminal imaging system 109 or may be in intermittent communication. For example, the two systems may be brought into temporary communication via a wired cable, or brought into communication via a wireless communication, or through any other suitable means at some point before, after, or during an examination. In addition, the processing system 106 may receive data such as x-ray images, annotated x-ray images, metrics calculated with the extraluminal imaging system 109, information regarding dates and times of examinations, types and/or severity of patient conditions or diagnoses, patient history or other patient information, or any suitable data or information from the extraluminal imaging system 109. The extraluminal imaging system 109 may also receive any of these data from the processing system 106. In some embodiments, and as shown in FIG. 1, the processing system 106 of system 100 and the extraluminal imaging system 109 may be in communication with a same, separate control system. In this embodiment, both systems may be in communication with the same display 108, processor, and/or communication interface as well as in communication with any other components implemented within the control system.

In some embodiments, the extraluminal imaging system 109 may be an x-ray imaging system and may include an x-ray imaging apparatus or device configured to perform x-ray imaging, angiography, fluoroscopy, radiography, or venography, among other imaging techniques. The x-ray imaging system 109 can generate a single x-ray image (e.g., an angiogram or venogram) or multiple (e.g., two or more) x-ray images (e.g., a video and/or fluoroscopic image stream) based on x-ray image data collected by the x-ray device. The x-ray imaging device may be a stationary x-ray system such as a fixed c-arm x-ray device, a mobile c-arm x-ray device, a straight arm x-ray device, or a u-arm device. The x-ray imaging device may additionally be any suitable mobile device. The x-ray system 106 may include a digital radiography device or any other suitable device.

The x-ray device may include an x-ray source and an x-ray detector mounted at a mutual distance with the anatomy of the patient or object to be imaged positioned between the source and detector. For example, the anatomy of the patient (including the vessel 120) can be positioned between the x-ray source and the x-ray detector. The x-ray source and detector may include any suitable components and may acquire x-ray images by any suitable means.

In some embodiments, the extraluminal imaging system 109 may be configured to obtain x-ray images without contrast. The extraluminal imaging system 109 may also be configured to obtain x-ray images with contrast (e.g., angiogram or venogram). In such embodiments, a contrast agent or x-ray dye may be introduced to a patient's anatomy before imaging. The contrast agent may also be referred to as a radiocontrast agent, contrast material, contrast dye, or contrast media. The contrast dye may be of any suitable material, chemical, or compound and may be a liquid, powder, paste, tablet, or of any other suitable form. For example, the contrast dye may be iodine-based compounds, barium sulfate compounds, gadolinium-based compounds, or any other suitable compounds. The contrast agent may be used to enhance the visibility of internal fluids or structures within a patient's anatomy. The contrast agent may absorb external x-rays, resulting in decreased exposure on the x-ray detector.

In some embodiments, the extraluminal imaging system 109 could be any suitable extraluminal imaging device, such as computed tomography (CT) or magnetic resonance imaging (MRI).

When the processing system 106 is in communication with the extraluminal imaging system 109, a communication interface may facilitate communication of signals between the processing system 106 and the extraluminal imaging device or extraluminal imaging system 109. This communication may include providing control commands to the x-ray source and/or the x-ray detector of the x-ray device and receiving data from the x-ray device. In some embodiments, the communication interface performs preliminary processing of the x-ray data prior to relaying the data to the processing system 106. In examples of such embodiments, the communication interface may perform amplification, filtering, and/or aggregating of the data. In an embodiment, the communication interface also supplies high- and low-voltage DC power to support operation of the extraluminal imaging device of the extraluminal imaging system 109 including circuitry within the device.

The processing system 106 receives the x-ray data from the extraluminal system 109 by way of the communication interface and processes the data to reconstruct an image of the anatomy being imaged. The processing system 106 outputs image data such that an image is displayed on the display 108. In an embodiment in which the contrast agent is introduced to the anatomy of a patient and a venogram is to be generated, the particular areas of interest to be imaged may be one or more blood vessels or other section or part of the human vasculature. The processing system 106 may be configured to receive an extraluminal image that was stored by the extraluminal imaging system 109 during a clinical procedure. The images may be further enhanced by other information such as patient history, patient record, IVUS imaging, pre-operative ultrasound imaging, pre-operative CT, or any other suitable data.

Figure 2:
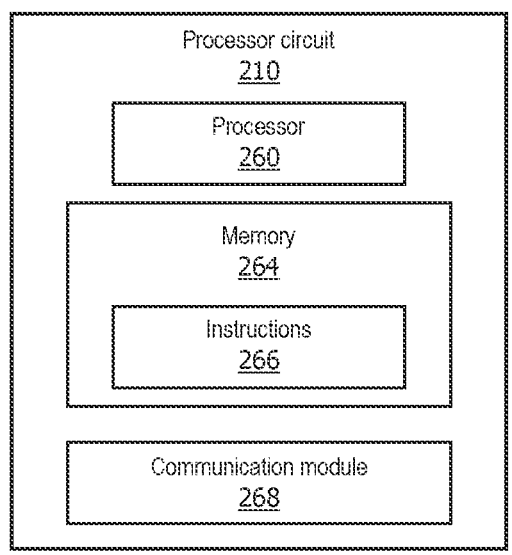
FIG. 2 is a schematic diagram of a processor circuit, according to aspects of the present disclosure.

FIG. 2 is a schematic diagram of a processor circuit, according to aspects of the present disclosure. The processor circuit 210 may be implemented in the processing system 106 of FIG. 1. In an example, the processor circuit 210 may be in communication with the intraluminal imaging device 102, the x-ray imaging system 109, and/or the display 108 within the system 100. The processor circuit 210 may include a processor and/or communication interface. One or more processor circuits 210 are configured to execute the operations described herein. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 260, cause the processor 260 to perform the operations described herein with reference to the probe 110 and/or the processing system 106 (FIG. 1). Instructions 266 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 268 can include any electronic circuitry and/or logic circuitry to facilitate direct or indirect communication of data between the processor circuit 210, the probe 110, and/or the display or monitor 108. In that regard, the communication module 268 can be an input/output (I/O) device. In some instances, the communication module 268 facilitates direct or indirect communication between various elements of the processor circuit 210 and/or the probe 110 (FIG. 1) and/or the host 130 (FIG. 1).

Figure 3:
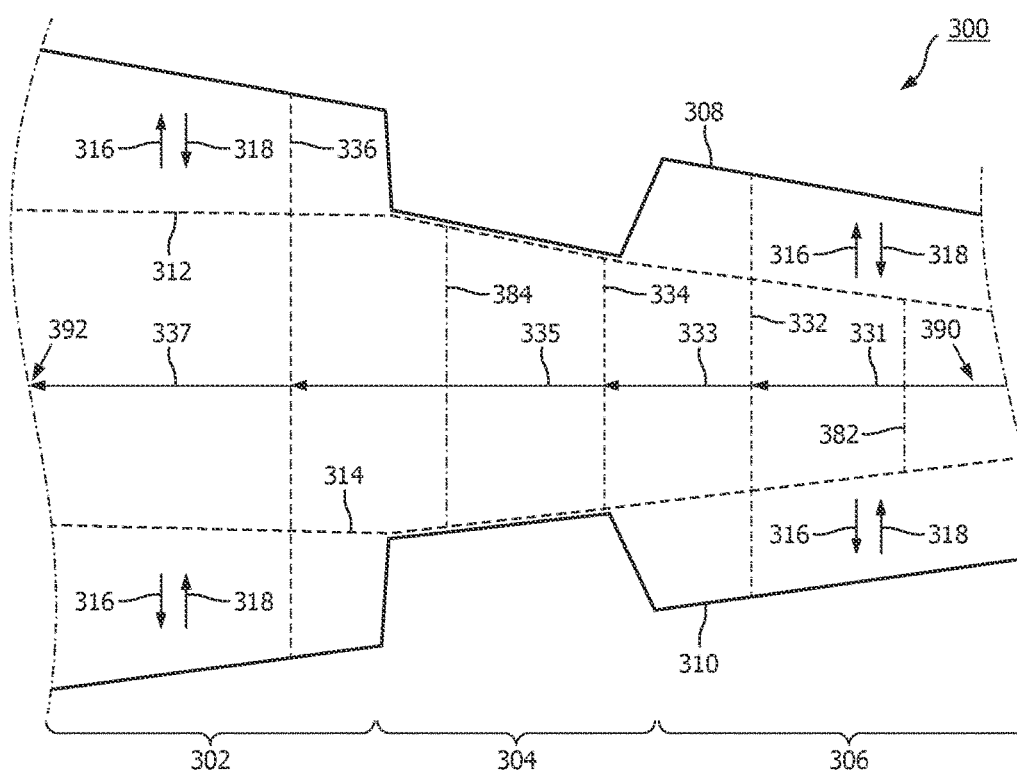
FIG. 3 is a diagrammatic cross-sectional side view of a section of an imaged vessel, according to aspects of the present disclosure.

FIG. 3 is a diagrammatic cross-sectional side view of a section of an imaged vessel 300, according to aspects of the present disclosure. FIG. 3 will be described in conjunction with the descriptions of FIGS. 4-7.

FIG. 3 depicts a diagrammatic view of a vessel 300. The vessel 300 shown may represent a stylized illustration of a peripheral vessel within a patient anatomy. However, the vessel 300 may be any other suitable body lumen within a patient. In some embodiments, the vessel 300 may be a deep vein located in a patient's hip, leg such as an upper thigh region, or similar vessel.

The vessel 300 shown in FIG. 3 includes a compressed region 304. On either side of the compressed region 304, the vessel includes healthy regions including a healthy distal region 306 and a healthy proximal region 302. The compressed region 304 may be a region along the vessel 300 of constricted blood flow. The compressed region 304 may be caused by any number of conditions. For example, the restricted blood flow at the compressed region 304 may be caused by a blockage within the vessel 300 such as a clot or build-up of plaque on the inner walls of the vessel, by hardening of the vessel walls, by a structure external to the vessel 300 compressing the vessel 300, or by any other cause.

The lines 308 and 310 in FIG. 3 may represent the walls of the vessel 300 or may define the areas of blood flow. For example, as shown by the lines 308 and 310, the cross-sectional area of the vessel 300 and/or the allowed blood flow through the vessel 300 may be increased along the healthy regions 302 and 306. However, along the compressed region 304, the cross-sectional area of the vessel 300, or the maximum allowable blood flow through the region 304, is decreased.

Regions of decreased blood flow within vessels, such as the compressed region 304 of the vessel 300 shown, may cause potentially dangerous symptoms within patients such as swelling, soreness, or pain. To remedy these, or other, symptoms or ailments, a physician must properly locate the compressed region 304. Such remedies may include deploying a stent, balloon, cryotherapy device, ablation device, drug delivery device, or any other treatment device or substance. To identify the location of the compressed region 304, a physician may use an IVUS imaging catheter. The catheter may be similar to the intravascular imaging device 102 described with reference to FIG. 1.

During the imaging procedure, patient movement from patient's breathing or other movement, may affect the acquired data. For example, as the patient breathes, the cross-sectional shape, area, and/or diameter (e.g., size) of the imaged vessel 300 changes. This change in vessel shape, area, and/or diameter is typically more drastic for healthy regions of the vessel 300, such as regions 302 and 306, and less drastic for blocked, compressed, or diseased regions, such as the compressed region 304. Specifically, as the patient exhales, a decrease in venous pressure causes the vessel 300 to expand as shown by arrows 316. This expansion of the vessel 300 causes the cross-sectional side view of the vessel to be shaped and/or sized similar to the lines 308 and 310 shown. As the patient inhales, an increase in venous pressure causes the vessel 300 to collapse or contract as shown by the arrows 318. As a result, the cross-sectional side view of vessel, or the area of allowable blood flow, is shaped and/or sized similar to the lines 312 and 314. Stated differently, patient expiration corresponds to an expansion of the vessel 300 and is illustrated by the lines 308 and 310 and patient inspiration corresponds to a collapse of the vessel 300 and is illustrated by the lines 312 and 314.

Because the vessel 300 expands and contracts more dramatically at healthy regions and less dramatically at compressed regions, the physician may use this phenomenon to confirm that image frames thought to be obtained from healthy regions of the vessel (e.g., regions 302 and/or 306), or reference frames, are in fact reference frames. The same phenomenon may help a physician ensure and that image frames thought to be obtained from compressed regions of the vessel (e.g., region 304), or target frames or compression frames, are indeed target frames. The physician may identify IVUS images or frames obtained by the catheter as showing healthy regions of vessel distal of the blockage, constricted or diseased regions at the blockage, and healthy regions of vessel proximal of the blockage. In addition, the constant expanding and contracting of the vessel 300 can result in inaccurate measurements of the vessel 300 depending on whether measurements were made during vessel expansion or contraction. These inaccuracies may lead to incorrect identification of reference frames or compression frames and may ultimately result in incorrect treatment decisions.

As an example, the line 382 shown at a location along the healthy region 306 represents a diameter of the vessel 300 after a complete patient inhalation. If the diameter of the vessel 300 at the location 382 was measured at this time, the diameter may be less than the measured diameter of the vessel 300 at a location along the compressed region 304. For example, the line 384 displayed in the compressed region 304 may correspond to a vessel diameter that is larger than the diameter measured at the location 382. Based on these measurements, the physician may incorrectly assume that the location 382 corresponds to a location of greater constriction or compression than the location 384. In this example, because the measurement of the location 382 was conducted after a complete inhalation, the physician may incorrectly conclude that the location 382 shows a constriction in the vessel 300. This incorrect conclusion may lead to incorrect treatment, such as a misplaced stent, the selection of a stent of the wrong diameter or length, or other mistakes in the choice of a therapeutic procedure.

As the physician images the length of the vessel 300, the physician and/or the system 100 may classify acquired IVUS images as potential reference frames or compression frames. A reference frame may be an IVUS image obtained along a healthy region of a vessel. The reference frame may be an IVUS image obtained along a healthy region of a vessel and obtained while the imaging catheter is stationary and while the patient takes a deep breath including a complete inhalation and exhalation, as will be described with more detail hereafter. The reference frame may be selected as the IVUS image obtained at this time and location showing the vessel at the greatest cross-sectional area or diameter. Similarly, a target frame may be an IVUS image obtained along a compressed, constricted, or diseased region of a vessel. A target frame may also be referred to as a compression frame. The compression frame may be an IVUS image obtained along a compressed region of a vessel and obtained while the imaging catheter is stationary and while the patient takes a deep breath including a complete inhalation and exhalation, as will be described hereafter. The compression frame may be selected as the IVUS image obtained at this time and location showing the vessel at the greatest cross-sectional area or diameter.

As the catheter is moved along the vessel, the system 100 may identify locations of potential reference frames or compression frames. The system 100 may also classify an IVUS image as a potential reference frame or a potential compression frame. The system 100 may identify locations of potential reference or target/compression frames and classify IVUS images as potential reference frames or potential compression frames according to some features similar to those described in U.S. Provisional Application No. 62/969,857, titled "Automatic Intraluminal Imaging-Based Target and Reference Image Frame Detection and Associated Devices, Systems, and Methods," and filed Feb. 4, 2020, which is hereby incorporated by reference in its entirety. To confirm that a potential reference or compression frame identified by the system 100 is indeed a reference or compression frame and to ensure that correct measurements are made at these locations, the methods described in FIGS. 4-7 may be employed.

Figure 4:
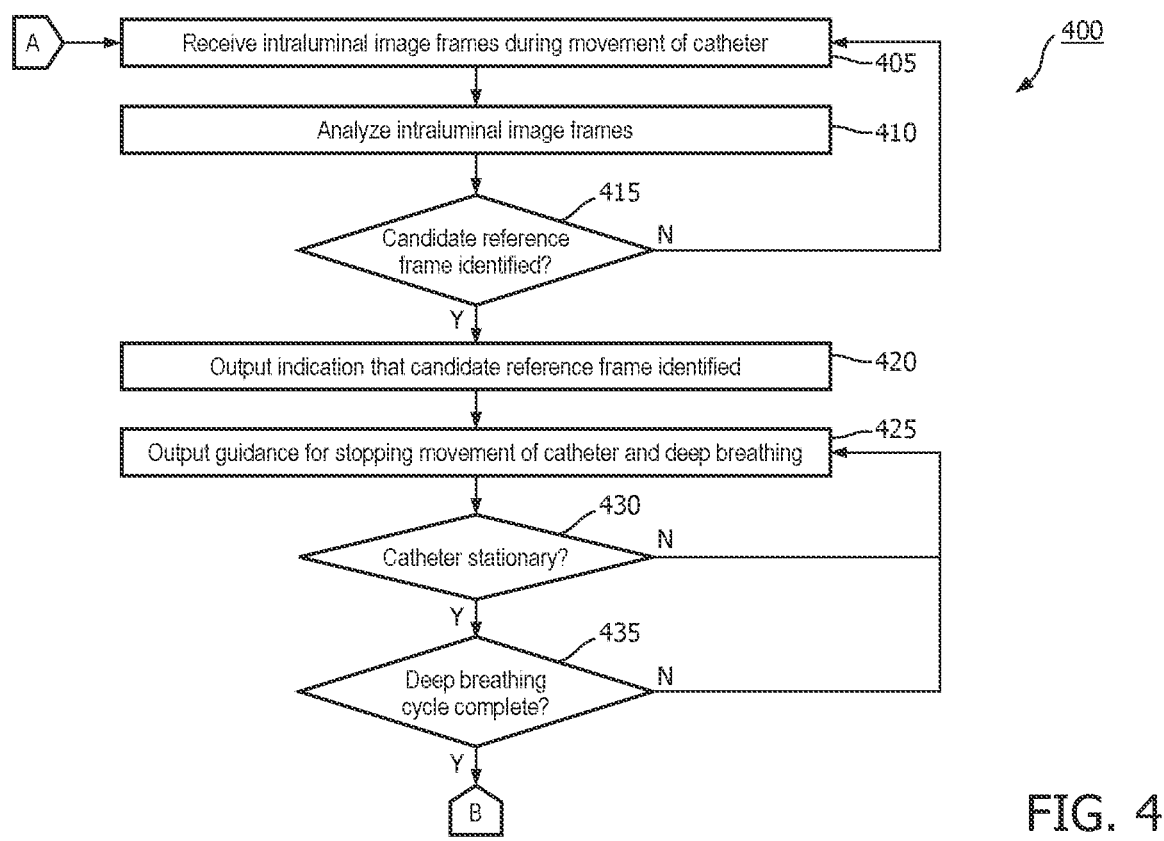
FIG. 4 is a flow diagram for a method of imaging a vessel during a patient deep breathing cycle at a location of a candidate reference frame, according to aspects of the present disclosure.

FIG. 4 is a flow diagram for a method 400 of imaging a vessel during a patient deep breathing cycle at a location of a candidate reference frame, according to aspects of the present disclosure. The method 400 will be described with reference to FIG. 3. As illustrated, the method 400 includes a number of enumerated steps, but embodiments of the method 400 may include additional steps before, after, or in between the enumerated steps. In some embodiments, one or more of the enumerated steps may be omitted, performed in a different order, or performed concurrently. The steps of the method 400 can be carried out by any suitable component within the system 100 and all steps need not be carried out by the same component. In some embodiments, one or more steps of the methods 400 can be performed by, or at the direction of, a processor circuit of the system 100 (e.g., the processor circuit 210 of FIG. 2), including, e.g., the processor 260 or any other component.

During an imaging procedure, the catheter may be positioned at a distal location 390 within the vessel 300 and moved proximally to a proximal location 392. In some embodiments, the catheter may be moved in an opposite direction. For example, the catheter may be positioned initially at the proximal location 392 and moved in a distal direction to the distal location 390.

At step 405, the method 400 includes receiving intraluminal image frames during the movement of the catheter. As the catheter moves from the location 390 to the location 392, it may continuously acquire intraluminal image frames depicting the vessel 300. These intraluminal image frames may be transmitted to the processing system 106 as described with reference to FIG. 1.

At step 410, the method 400 includes analyzing the acquired intraluminal image frames. The system 100 may perform any suitable analysis of the received intraluminal image frames. For example, the system 100 may apply various image processing techniques such as edge identification, pixel-by-pixel analysis to determine transition between light pixels and dark pixels, filtering, or any other suitable techniques to identify relevant structures or locations within the received image frames. The system 100 may also employ various machine learning techniques. The system 100 may also perform measurements of received image frames to determine metrics such as a vessel diameters, distances, cross-sectional areas, blood flow, etc., At step 415, the method 400 includes determining whether a candidate reference frame has been identified. As the catheter moves from the distal location 390 to the proximal location 392, or in some embodiments, from the proximal location 392 to the distal location 390, an IVUS image or frame corresponding to a particular location may be identified. This identification may be determined as previously described with reference to FIG. 3. At the step 415, the system 100 may classify the selected IVUS image frame as a candidate reference frame. In the example shown in FIG. 3, such a location may be illustrated by the location 332. The catheter may be moved from the starting location 390 along the vessel as shown by the arrow 331 to the location 332. In some instances, the system 100 may determine that the received IVUS image corresponding to the location 332 does not correspond to a candidate reference frame. In this instance, the method 400 may revert to step 405 and movement of the catheter may continue in a proximal direction and additional IVUS images may be acquired at step 405 and analyzed at step 410. In an example that the system 100 determines that a candidate reference frame has been identified at the exemplary location 332, the method 400 proceeds to step 420.

At step 420, the method 400 includes outputting an indication that a candidate reference frame has been identified. This output may include a visual, audio, or other signal to the user of the system 100. For example, the output may include text displayed on the monitor 108 (FIG. 1) stating that a candidate reference frame has been identified. The output may include an illustration, symbol, animation, or any other suitable visual representation including any alphanumeric symbols. The output may be accompanied by an auditory signal of any type as well.

At step 425, the method 400 includes outputting guidance to the user of the system 100 to stop movement of the catheter and instruct the patient to begin breathing deeply. Breathing deeply may include alternating one or more deep inhales and exhales. Breathing deeply may include alternating inspiration and expiration. For example, the patient may be instructed to breathe in deeply, then breathe out deeply, then breathe in deeply, then breathe out deeply, and so on. The guidance output may be of any suitable type including any of those described at step 420.

The system 100 may direct the patient to breathe deeply to ensure accurate confirmation of the candidate reference frame. The extent to which the imaged vessel expands or contracts while the patient breathes is dependent on the depth of the patient breath as well as the region of the vessel (e.g., whether the region is a healthy region or a compressed region). For example, as a patient breathes shallowly, the amount of change in vessel shape, size, and/or diameter observed by the catheter is less. By contrast, as the patient breathes deeply, the amount of change in vessel shape, size, and/or diameter is greater. To produce the maximum amount of change in vessel shape, size, and/or diameter caused by the patient breathing, the patient should be instructed to breathe deeply during the measurement of a location of a candidate reference or compression frame.

In some embodiments, the guidance for stopping movement of the catheter and for the patient to being deep breathing cycle may be a selectable setting available to a user of the system. For example, a user of the system may direct the system to output the guidance for stopping the movement of the catheter and deep breathing if a candidate reference frame has been identified. In some embodiments, the user may direct the system to not output the guidance for stopping the movement of the catheter and deep breathing if a candidate reference frame has been identified. In some embodiments, the system may prioritize various steps or functions. For example, the system may prioritize rejecting a false target candidate reference frame over confirming a correctly identified candidate reference frame.

At step 430, the method includes verifying that the catheter is stationary. The system 100 may employ any suitable method of detecting movement of the catheter and/or verifying that the catheter is stationary at step 430. For example, a processor circuit can use feature tracking within the intraluminal images, e.g., based on if the feature(s) change within the intraluminal images. For example, in peripheral venous applications, the feature can be the quantity of vessels/lumens in the intraluminal images. The intraluminal imaging catheter can be in the vein and obtain image data of the vein, as well as neighboring arteries/veins. If the intraluminal image catheter is stationary, the quantity of vessels/lumens will remain the same in the plurality of intraluminal images obtained by the imaging catheter. If the intraluminal imaging catheter is moving, the quantity of vessel/lumens will change in the imaging catheter. In some embodiments, the system 100 may can use of speckle tracking in the intraluminal images to determine whether the catheter is stationary. Alternatively, the system 100 may receive extraluminal images from the extraluminal imaging system 109 and coregister received IVUS images to locations along the vessel as shown in corresponding extraluminal images according to principles of coregistration. Aspects of the present disclosure can include coregistration features similar to those described in U.S. Pat. No. 7,930,014, titled "Vascular Image Co-Registration," which is hereby incorporated by reference in its entirety.

If the system determines that the catheter is stationary, the method 400 may progress to step 435. If, however, the system 100 determines that the catheter is not stationary, but is still moving, the method 400 may revert back to step 425. At step 425, the system 100 may again display or continue to display guidance to stop movement of the catheter. This output may also include guidance to instruct the patient to begin deep breathing or may not.

At step 435, the method includes verifying that the patient has completed a deep breathing cycle. A deep breathing cycle may be defined as a patient performing a complete exhale followed by a complete inhale or vice versa. The system 100 may determine that a deep breathing cycle has been completed based on the change in vessel shape and diameter or size as observed by the intravascular imaging device. Additional details of this determination will be described with reference to FIG. 9. After the system 100 determines that a deep breathing cycle has been completed, the method 400 may proceed to step 505 of the method 500 as shown by the off-page symbol B of FIG. 4. If, however, the system 100 determines that a deep breathing cycle has not been completed, the system may revert to step 425 and guidance to begin or continue deep breathing may again be displayed or may continue to be displayed. This guidance may be accompanied by guidance to stop movement of the catheter or may not be.

It is noted that the steps 430 and 435 may performed in any suitable order. For example, the steps 430 and 435 may be conducted simultaneously or separately. The step 435 may be performed prior to the step 430 or vice versa. In addition, if the step 430 has been satisfied (e.g., the system has determined that the catheter is stationary), but the step 435 is not met (e.g., a deep breathing cycle has not been completed), the system may revert to step 425 to display guidance and skip the step 430 and proceed to step 435 to verify that a deep breathing cycle has been completed. Because the system has already determined that the catheter is stationary, it may not reperform step 430.

Figure 5:
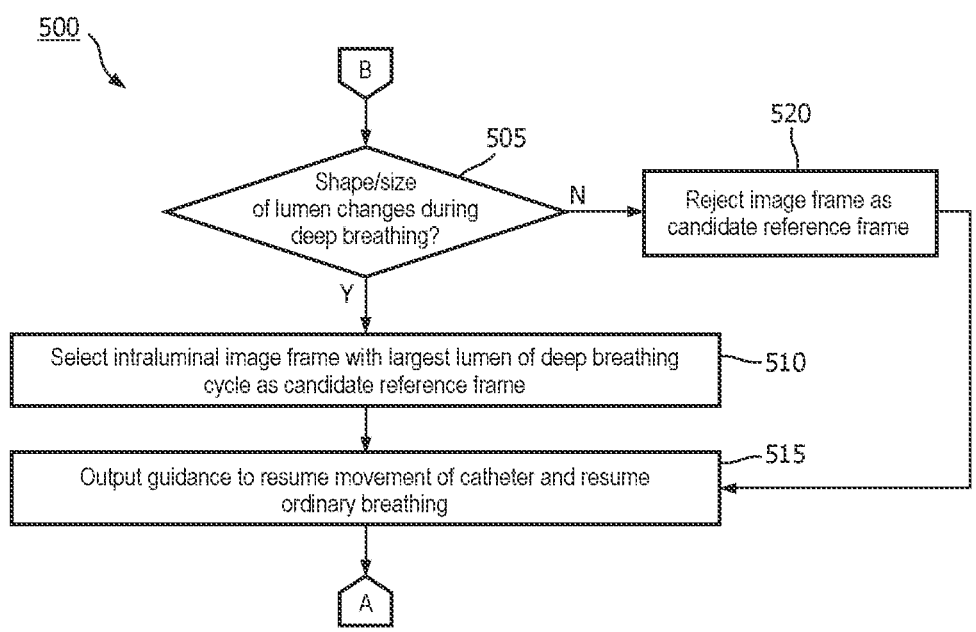
FIG. 5 is a flow diagram for a method of confirming or rejecting a candidate reference frame, according to aspects of the present disclosure.

Referring now to FIG. 5, FIG. 5 is a flow diagram for a method 500 of confirming or rejecting a candidate reference frame, according to aspects of the present disclosure. As illustrated, the method 500 includes a number of enumerated steps, but embodiments of the method 500 may include additional steps before, after, or in between the enumerated steps. In some embodiments, one or more of the enumerated steps may be omitted, performed in a different order, or performed concurrently. The steps of the method 500 can be carried out by any suitable component within the system 100 and all steps need not be carried out by the same component. In some embodiments, one or more steps of the methods 500 can be performed by, or at the direction of, a processor circuit of the system 100 (e.g., the processor circuit 210 of FIG. 2), including, e.g., the processor 260 or any other component.

At step 505, the method 500 includes determining whether the shape and/or size of the lumen changes during the deep breathing cycle performed at steps 425 and/or 435. Referring back to FIG. 3, the at least one deep breathing cycle may be performed at the location shown by the line 332. The catheter may be held stationary, as described, at this location 332 throughout at least one full deep breathing cycle. The catheter may obtain IVUS images throughout this breathing cycle. Each received IVUS image frame may be analyzed according to the previously described techniques to determine the cross-sectional shape and diameter of the vessel in each received image. As the deep breathing cycle is completed, the physician may observe that the walls of the vessel move from the locations shown by the lines 308 to the locations shown by the lines 312 and 314 and back again.

Based on this change in vessel shape and/or size, the system 100 may proceed from step 505, referring again to FIG. 5, to step 510.

At step 510, the method 500 includes selecting the intraluminal image frame with the largest lumen of the images obtained during the deep breathing cycle as a candidate reference frame. Referring back to FIG. 3, at the location 332, the catheter obtains several IVUS images at this same location throughout the deep breathing cycle. As the deep breathing cycle is completed, the lumen shape and/or size is seen to expand as the patient exhales and to contract as the patient inhales. The lumen cross-sectional area may be calculated for each received image and the image showing a lumen with the largest cross-sectional area may be selected as the candidate reference frame associated with the location 332. This selected image may be reviewed by the physician. The physician may then confirm that selected IVUS image frame is indeed the frame of largest lumen cross-sectional area and that the location corresponds to a reference frame confirming that it was obtained at a healthy region of the vessel. Advantageously, the candidate frame can be confirmed as the reference frame in real time or near real time during the intraluminal imaging procedure (e.g., while the intraluminal images as being obtained by the intraluminal imaging device, such as during the pullback).

Referring to FIG. 5, at step 515, the method 500 includes outputting guidance to resume movement of the catheter and resume ordinary breathing. This guidance may be conveyed by any suitable method including those previously described. The physician may continue to move the catheter along the vessel from the location 332 (FIG. 3) in a proximal direction toward the location 392. The physician may also instruct the patient to stop deep breathes and to breath normally.

Referring back to step 505 of FIG. 5, the system may determine that shape of lumen does not change sufficiently. This determination may be based on the change of shape of the lumen observed in the IVUS images obtained at the location 332 (FIG. 3) throughout a deep breathing cycle. In some embodiments, the required amount of change of vessel shape at a location of a candidate reference frame may be determined by a threshold amount of change. For example, the system may determine two diameters of the vessel at the location 332. One diameter may be the distance between the inner walls of the vessel along one axis and the other diameter may be the distance between the inner walls of the vessel along a second axis perpendicular to the first axis, as will be described in more detail with reference to FIGS. 10A and 10B. In one example, the threshold amount of change of shape may correspond to a threshold change in either of these diameters. For example, if the diameter along either axis decreases or increases by a certain percentage at any point during the deep breathing cycle, the system may determine that the location corresponds to a reference frame and (referring to FIG. 5) may proceed from step 505 to step 510. If, however, this threshold percentage of change for either diameter is not met, the system may determine that location does not correspond to a reference frame and may proceed to step 520. The threshold amount of change may also be defined by other metrics or measurements. For example, the threshold may correspond to an amount of change in cross-sectional area. Other metrics may include changes in the curvature of the vessel walls, the length of the cross-sectional perimeter of the vessel walls, or any other metric associated with a change of cross-sectional shape of the lumen. The change and associated threshold may be measured as a percentage, as a measurement of length, area, or by any other metric.

The threshold amount of change of a vessel may be determined by the system or by a user of the system. The threshold amount of change may depend on circumstantial factors such as the particular vessel or other lumen measured, its location within the patient, whether the location imaged is distal or proximal to a blockage, constriction, or compression region, observed conditions of the vessel imaged, physiological attributes of the patient, biographical attributes of the patient such as age, weight, etc., or any other factors.

At step 520, the method 500 includes rejecting the image frame as a candidate reference frame. This may occur if the system determines that the threshold amount of change of lumen shape was not met at step 505. Advantageously, the candidate frame can be rejected as the reference frame in real time or near real time during the intraluminal imaging procedure (e.g., while the intraluminal images as being obtained by the intraluminal imaging device, such as during the pullback). After the image frame is rejected at step 520, the system may skip step 510 and proceed to step 515 indicating to the physician to resume movement of the catheter and for the patient to resume ordinary breathing. After the step 515, as shown by the off-page symbol A, the system may revert back to step 405 of FIG. 4. In the example shown in FIG. 3, the physician may continue to move the catheter in a proximal direction from the location 332.

Referring again to FIG. 3, the physician may move the catheter from the location 332 in a proximal direction as shown by the arrow 333 to a new position 334. As the physician moves the catheter, the catheter may continue to acquire IVUS images and the system may continue to analyze those images to determine whether a location of a reference or compression frame is identified.

At the location shown by the line 334, a received IVUS image frame may be identified as a potential compression frame according to principles described with reference to FIG. 3. When a potential compression frame is selected, the system may perform the method 600 of FIG. 6.

Figure 6:
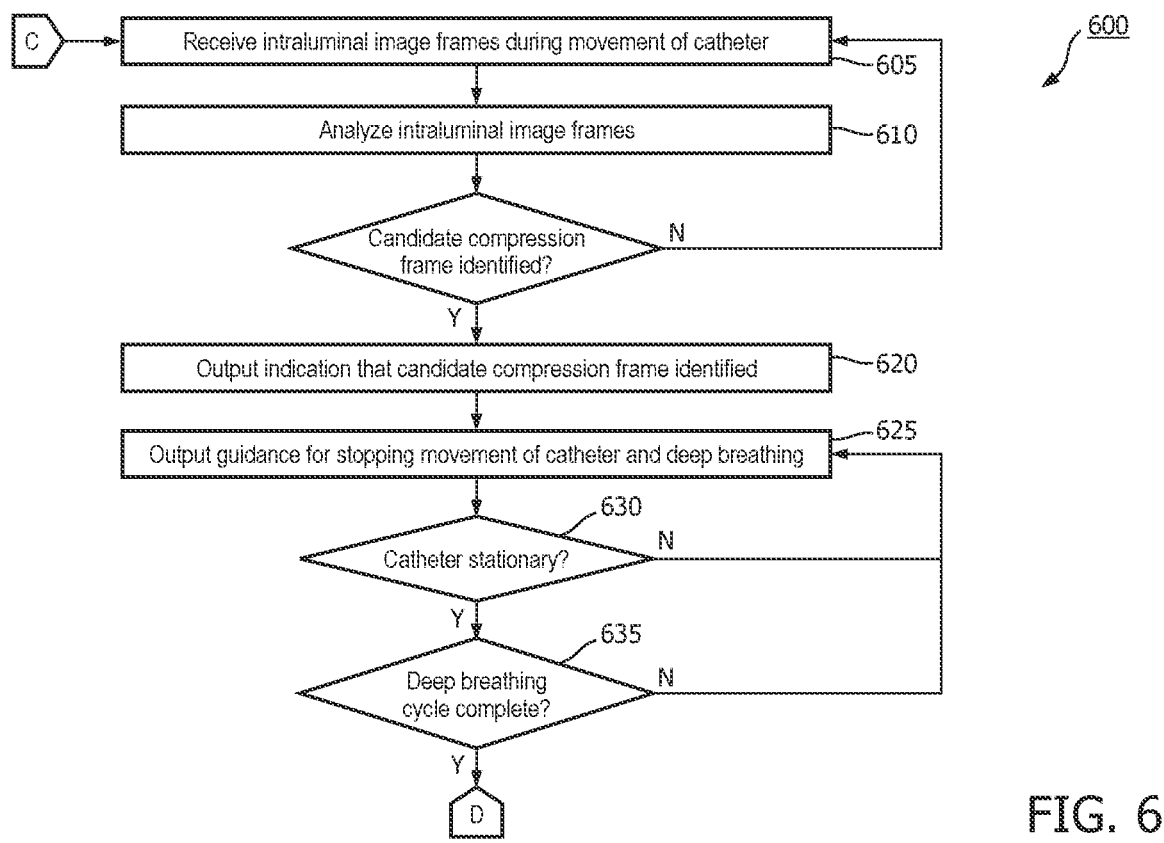
FIG. 6 is a flow diagram for a method of imaging a vessel during a patient deep breathing cycle at a location of a candidate compression frame, according to aspects of the present disclosure.

FIG. 6 is a flow diagram for a method 600 of imaging a vessel during a patient deep breathing cycle at a location of a candidate compression frame, according to aspects of the present disclosure. As illustrated, the method 600 includes a number of enumerated steps, but embodiments of the method 600 may include additional steps before, after, or in between the enumerated steps. In some embodiments, one or more of the enumerated steps may be omitted, performed in a different order, or performed concurrently. The steps of the method 600 can be carried out by any suitable component within the system 100 and all steps need not be carried out by the same component. In some embodiments, one or more steps of the methods 600 can be performed by, or at the direction of, a processor circuit of the system 100 (e.g., the processor circuit 210 of FIG. 2), including, e.g., the processor 260 or any other component.

Steps 605 and 610 of the method 600 may be substantially similar to the steps 405 and 410 of the method 400 described with reference to FIG. 4. Specifically, as the catheter is moved from the location 332 to 334 (FIG. 3), it may continue to acquire intraluminal image frames and the system may continue to analyze those image frames.

At step 615, the method 600 includes determining whether a candidate compression frame has been identified. As the catheter moves from the distal location 390 to the proximal location 392, an IVUS image or frame corresponding to a particular location may be identified. This identification may be determined as previously described with reference to FIG. 3. At the step 615, the system 100 may classify the selected IVUS image frame as a candidate compression frame. In the example shown in FIG. 3, such a location may be illustrated by the location 334. In some instances, the system may determine that the received image frame of the location 334 does not correspond to a candidate compression frame. In this instance, the method 600 may revert to step 605 and movement of the catheter may continue in a proximal direction and additional intraluminal image frames may be acquired at step 605 and analyzed at step 610. In the instance that the system 100 determines that a candidate compression frame has been identified, the method 600 proceeds to step 620.

At step 620, the method 600 includes outputting an indication that a candidate compression frame has been identified. The step 620 may be substantially similar to the step 420 of the method 400 (FIG. 4) except the output conveys that a compression frame, rather than a reference frame, has been identified.

The steps 625 through 635 of the method 600 are identical to the step 425 through 435 of the method 400 (FIG. 4). The description of steps 425 through 435 apply to the steps 625 through 635. At the completion of step 635, or in other words, after the system has determined that the catheter is stationary and one complete breathing cycle has been performed, the system may proceed to step 715 of FIG. 7 as shown by the off-page symbol D.

Figure 7:
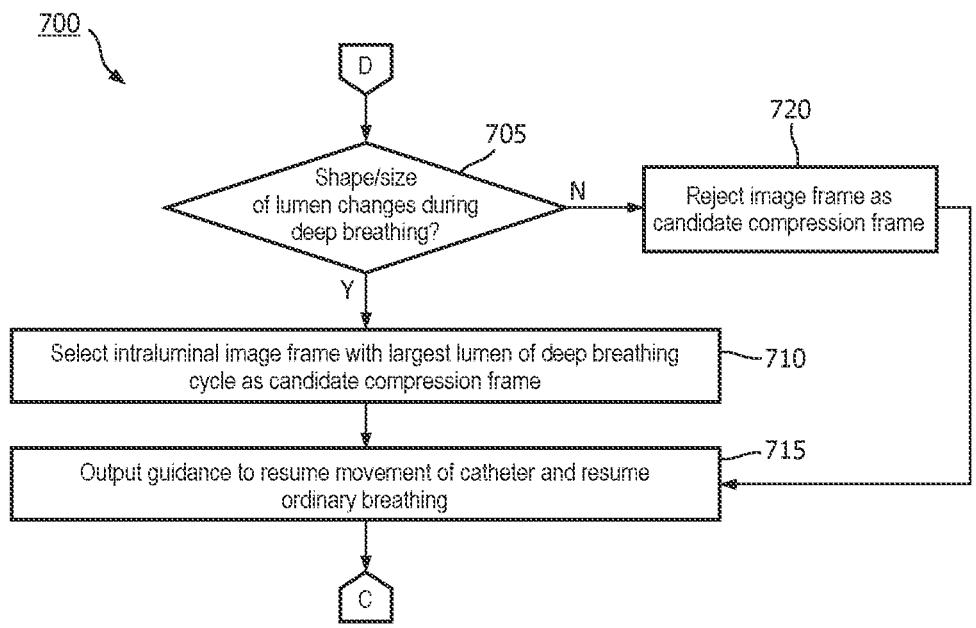
FIG. 7 is a flow diagram for a method of confirming or rejecting a candidate compression frame, according to aspects of the present disclosure.

FIG. 7 is a flow diagram for a method 700 of confirming or rejecting a candidate compression frame, according to aspects of the present disclosure. As illustrated, the method 700 includes a number of enumerated steps, but embodiments of the method 700 may include additional steps before, after, or in between the enumerated steps. In some embodiments, one or more of the enumerated steps may be omitted, performed in a different order, or performed concurrently. The steps of the method 700 can be carried out by any suitable component within the system 100 and all steps need not be carried out by the same component. In some embodiments, one or more steps of the methods 700 can be performed by, or at the direction of, a processor circuit of the system 100 (e.g., the processor circuit 210 of FIG. 2), including, e.g., the processor 260 or any other component. FIG. 7 will be described in conjunction with a description of aspects of FIG. 3.

At step 705, the method 700 includes determining whether the shape of the lumen changes during the deep breathing cycle performed at steps 625 and/or 635. Referring back to FIG. 3, the at least one deep breathing cycle may be performed at the location shown by the line 334. The step 705 is substantially similar to the step 505 of the method 500 (FIG. 5) described previously. Specifically, each intraluminal image frame received from the location 334 through a deep breathing cycle is analyzed to determine the amount of change of cross-sectional shape and diameter. The physician and/or system may observe that the walls of the vessel do not change or move, or do not change or move a great amount. Based on this lack of change or small amount of change in vessel shape, the system 100 may proceed from step 705, referring again to FIG. 7, to step 710.

At step 710, the method 700 includes selecting the intraluminal image frame with the largest lumen of the images obtained during the deep breathing cycle as a candidate compression frame. This selected image may be reviewed by the physician. The physician may confirm that selected image frame is indeed the frame of largest lumen cross-sectional area and that the location corresponds to a compression frame confirming that it was obtained at a compressed region of the vessel. Advantageously, the candidate frame can be confirmed as the target/compression frame in real time or near real time during the intraluminal imaging procedure (e.g., while the intraluminal images as being obtained by the intraluminal imaging device, such as during the pullback).

At step 715, the method 700 includes outputting guidance to resume movement of the catheter and resume ordinary breathing. This guidance may be conveyed by any suitable method including those previously described.

Referring back to step 705, the system may determine that shape of lumen does change sufficiently. This determination may be based on the change of shape of the lumen observed in the intraluminal images obtained at the location 334 (FIG. 3). In this case, the amount of change may exceed a threshold amount of change. As previously described, this threshold amount of change may be determined based on two diameter measurements of differing axes, changes in cross-sectional area, or by any other method previously described. Changes observed at a location of a compression frame are described with more detail with reference to FIGS. 11A-11B hereafter.

The threshold amount of change of a vessel at step 705 may be the same threshold as that described with reference to step 505 of the method 500 (FIG. 5) or may differ. The threshold may be determined by the system or by a user of the system and may depend on any of the circumstantial factors described with reference to step 505 of method 500.

At step 720, the method 700 includes rejecting the image frame as a candidate compression frame. This may occur if the system determines that the threshold amount of change of lumen shape was exceeded at step 705. Advantageously, the candidate frame can be rejected as the target/compression frame in real time or near real time during the intraluminal imaging procedure (e.g., while the intraluminal images as being obtained by the intraluminal imaging device, such as during the pullback). After the image frame is rejected at step 720, the system may skip step 710 and proceed to step 715 indicating to the physician to resume movement of the catheter and for the patient to resume ordinary breathing. After the step 715, as shown by the off-page symbol C, the system may revert back to step 605 of FIG. 6. In the example shown in FIG. 3, the physician may continue to move the catheter in a proximal direction from the location 334.

Referring again to FIG. 3, as the physician continues to move the catheter in a proximal direction from the location 334, the catheter may continue to acquire image frames and the system may continue to analyze those image frames according to steps 405 and 410 of the method 400 (FIG. 4) and/or steps 605 and 610 of the method 600 (FIG. 6). In the example shown in FIG. 3, the physician may move the catheter according to the arrow 335 from the position 334 to a position proximal to that, the position 336. At the location 336, the system may identify the location as one corresponding to a candidate reference frame. As shown in FIG. 3, the location 336 is within the proximal healthy region 302.

In response to the identification of a location of a potential candidate reference frame, the system may again perform the methods 400 and 500. For example, the system may determine at step 415 of the method 400 (FIG. 4) that a candidate reference frame has been identified. At steps 420 through 435, the system may output that a candidate reference frame has been identified, output guidance to stop movement of the catheter and begin deep breathing, and confirm that those actions have been taken. Referring to FIG. 5, at step 505, the system may observe a change of shape of the lumen exceeding the threshold described previously and select the image frame of largest lumen as the candidate reference frame at step 510. At step 515, the system may output guidance to resume movement and normal breathing. Referring back to FIG. 3, the physician may then proceed to move the catheter along the arrow 337 to the most proximal location 392 and complete the imaging procedure.

It is understood that the example shown in FIG. 3 and described herein with reference to FIG. 3 is merely illustrative. The system 100 may identify any number of locations associated with a potential candidate reference frame or potential candidate compression frame at any point along the imaged vessel. At any of these locations, the system 100 may perform methods 400 and 500 of FIGS. 4 and 5 or methods 600 and 700 of FIGS. 6 and 7 depending on the identification of a reference or compression frame. In addition, during an imaging procedure, the physician may alter the direction of movement of the catheter in any suitable way. For example, the physician may begin a procedure by moving the catheter in a proximal direction and then move the catheter in a distal direction at any point(s) in time during the procedure.

Figure 8:
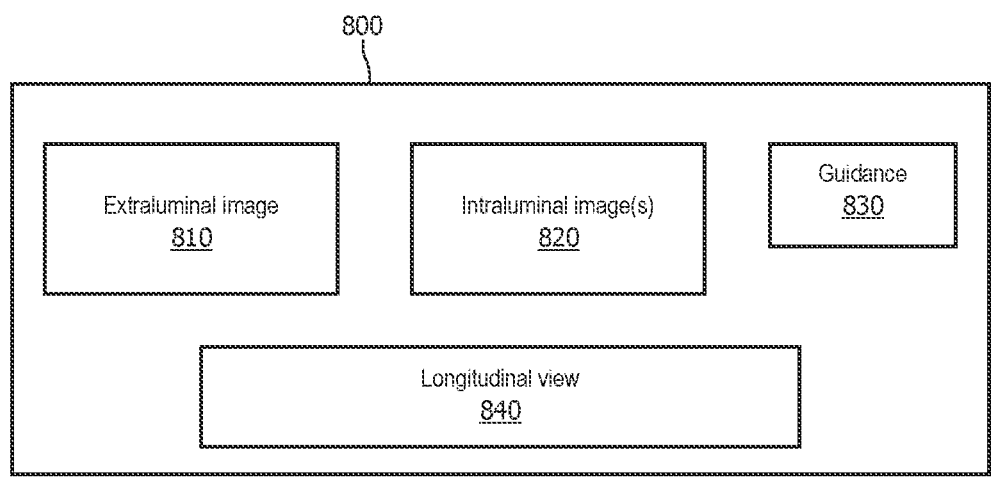
FIG. 8 is a diagrammatic view of a graphical user interface displaying an intraluminal image coregistered to an extraluminal image for identification of a reference or compression frame, according to aspects of the present disclosure.

In some embodiments, the physician may instruct the system to perform any aspects of the methods 400, 500, 600, or 700 without the system having identified a location of a potential candidate reference or compression frame. For example, the physician may identify a particular region of interest which he or she wishes to measure through a deep breathing cycle. The physician may indicate to the system to perform some aspects of the methods listed and determine whether the location corresponds to a candidate reference frame or a candidate compression frame. Additionally, the physician may direct the system, before the imaging procedure, for example by manipulating various settings of the system, to perform various aspects of methods 400, 500, 600, and/or 700 after a bookmark is placed during a pullback imaging procedure. In some embodiments, a user of the system may direct the system, before an imaging procedure, to perform various aspects of methods 400, 500, 600, and/or 700 after a target pullback is placed. FIG. 8 is a diagrammatic view of a graphical user interface displaying an intraluminal image coregistered to an extraluminal image for identification of a reference or compression frame, according to aspects of the present disclosure. The graphical user interface 800 may include an extraluminal image 810, an intraluminal image 820, a longitudinal view 840 of the vessel, and a display of user guidance 830. The longitudinal view 840 can be an ILD, such as an in line digital or image longitudinal display.

The extraluminal image 810 may be displayed to a user of the system 100 within the graphical user interface 800. The extraluminal image 810 may be acquired with the extraluminal imaging system 109 and may be received by the processor 106 of the system 100 (FIG. 1). The extraluminal image 810 may be an x-ray image. The extraluminal image 810 may be an x-ray image acquired during an imaging procedure in which no contrast agent is introduced to the patient vasculature or in which contrast agent is introduced. The image 810 may be one of many extraluminal images acquired in a continuous image stream. The extraluminal image 810 may be an x-ray fluoroscopy image. In other embodiments, different types of extraluminal images may be used as previously described. The extraluminal image 810 provides the user with a view of a region of the patient anatomy through which the intravascular device 102 moved during an imaging procedure.

In some embodiments, the extraluminal image 810 shown in the interface 800 is one of the x-ray images obtained by the extraluminal imaging system 109 during the IVUS pullback procedure. In other embodiments, however, the extraluminal image 810 may not be one of the extraluminal images obtained during the pullback procedure. For example, the extraluminal image 810 may be any suitable image acquired of the same region of the patient with a guidewire positioned within the same vessel imaged. In such an embodiment, the extraluminal image 810 may be acquired from a similar angle as the extraluminal images acquired during the procedure such that the shape, placement, orientation, and general appearance of the guidewire within the image 810 is similar to the pathway defined by the movement of the intravascular device 102 during the imaging procedure.

The system 100 may receive from the x-ray imaging system 109 a plurality of extraluminal images. Some of these images may have been acquired as the pullback procedure was performed. In other words, some of the received extraluminal images may have been received while the intravascular device 102 (FIG. 1) was acquiring intraluminal images. However, some extraluminal images received may not have been acquired during the pullback procedure. Rather, some may have been acquired before or after the pullback procedure.

In some embodiments, the extraluminal image 810 may include a depiction of a radiopaque portion of the intravascular device 102 (FIG. 1). Because the intravascular device 102 is constructed of radiopaque material, it may be visible in the image 810 acquired. For example, the portion of the intravascular device 620 that is visible in the extraluminal image 810 can be the imaging assembly (e.g., transducer assembly) and/or radiopaque markers.

The graphical user interface 800 may correspond to a display presented to the user of the system 100 during or after a pullback procedure. A pullback procedure may include an imaging procedure in which the intravascular device 102 is moved through the patient anatomy along a guidewire within a lumen while the x-ray imaging system 109 simultaneously acquires fluoroscopy images of the same region of the patient anatomy without contrast agent inside the vessel. Markers may be included overlaid over the extraluminal image 810 to indicate a starting position, ending position, and current position of the intravascular device 102 (FIG. 1) at various points throughout the pullback procedure. In some embodiments, a pathway is also shown overlaid over the extraluminal image 810. The pathway may be determined and generated by the system 100 based on the locations of the radiopaque portion of the intravascular device 102 within the extraluminal images acquired by the x-ray imaging system 151. The location of the device 102 (FIG. 1) may be determined by the system 100 using any above-mentioned image processing or deep learning techniques for each acquired x-ray image. These locations may together define the shape of the pathway overlaid over the image 810.

The process of coregistering intravascular data to locations within the extraluminal image 810 along the guidewire may include first co-registering the data to the pathway.

The graphical user interface 800 additionally depicts a longitudinal view or ILD 840. The intraluminal images acquired with the device 102 (FIG. 1), may be used to create an ILD 840, shown adjacent to the intraluminal image 820. In that regard, the ILD 840 is a tomographic or radial cross-sectional view of the blood vessel. The ILD 840 provides a longitudinal cross-sectional view of the blood vessel. The ILD 840 can be a stack of the intraluminal images acquired at various positions along the vessel, such that the longitudinal view of the ILD 840 is perpendicular to the radial cross-sectional view of the intraluminal image. In such an embodiment, the ILD 840 may show the length of the vessel, whereas an individual intraluminal image 820 is a single radial cross-sectional image at a given location along the length. In another embodiment, the ILD 840 may be a stack of the intraluminal images acquired overtime during the imaging procedure and the length of the ILD 840 may represent time or duration of the imaging procedure. The ILD 840 may be generated and displayed in real time or near real time during the pullback procedure. As each additional intraluminal image 820 is acquired by the device 102 (FIG. 1), it may be added to the ILD 840. For example, at a point in time during the pullback procedure, the ILD 840 shown in FIG. 8 may be partially complete. In some embodiments, the processor circuit may generate an illustration of a longitudinal view of the vessel being imaged based on the received IVUS images. For example, rather than displaying actual vessel image data as the ILD 840 does, the illustration may be a stylized version of the vessel, with e.g., continuous lines showing the lumen border and vessel border. The ILD 840 may include an indicator identifying the location along the ILD 840 at which the intraluminal image 820 currently displayed was obtained.

The processor circuit 106 (FIG. 1) may move the indicator by any suitable method or in response to any type of user input. For example, the user may use a mouse to click on a location within the extraluminal image 810, may touch a location within the extraluminal image 810 using a touch-screen device, or may indicate the location by any other way. For example, the user may input any commands to the system 100 via a mouse, a mouse click, cursor, pointer, joystick, physical button, pressure of depressing a physical button, a control pad, finger or touch of the finger on a screen, with a stylus or touch of a stylus on a screen, or by any other means. Whatever the input device, the input device may be positioned proximate to or spaced from the patient. For example, the input device could be a bedside controller coupled to a rail of a bed or table upon which the patient is positioned. The input device may be in a control room separate from the patient and proximate to the procedure room. In some embodiments, the user may select and drag the indicator within either the extraluminal image 810 or longitudinal view 840 to a different location to show the intraluminal image obtained at the new location.

In some embodiments, guidance 830 may be displayed to the user within the graphical user interface 800. For example, a portion of the interface may be used to convey output messages to the user. The guidance 830 may be displayed adjacent to the intraluminal image 820 as shown in FIG. 8. The guidance 830 may be displayed at any other location within the interface 800 as well. For example, it could be adjacent to any other element of the interface 800 or may be completely or partially overlaid over any other elements of the interface 800. As stated previously, this guidance 830 may be used at steps 420 and 425 of the method 400 (FIG. 4), step 515 of the method 500 (FIG. 5), steps 620 and 625 of the method 600 (FIG. 6), or step 715 of the method 700 (FIG. 7). The guidance 830 may convey to a user to stop movement of the catheter, begin movement of the catheter, to instruct a patient to begin deep breathing, or to instruct a patient to stop deep breathing and resume regular breathing. The guidance 830 may include any other suitable instructions or guidance as well and may convey this information by any suitable method including those described with reference to FIG. 4.

Figure 9:
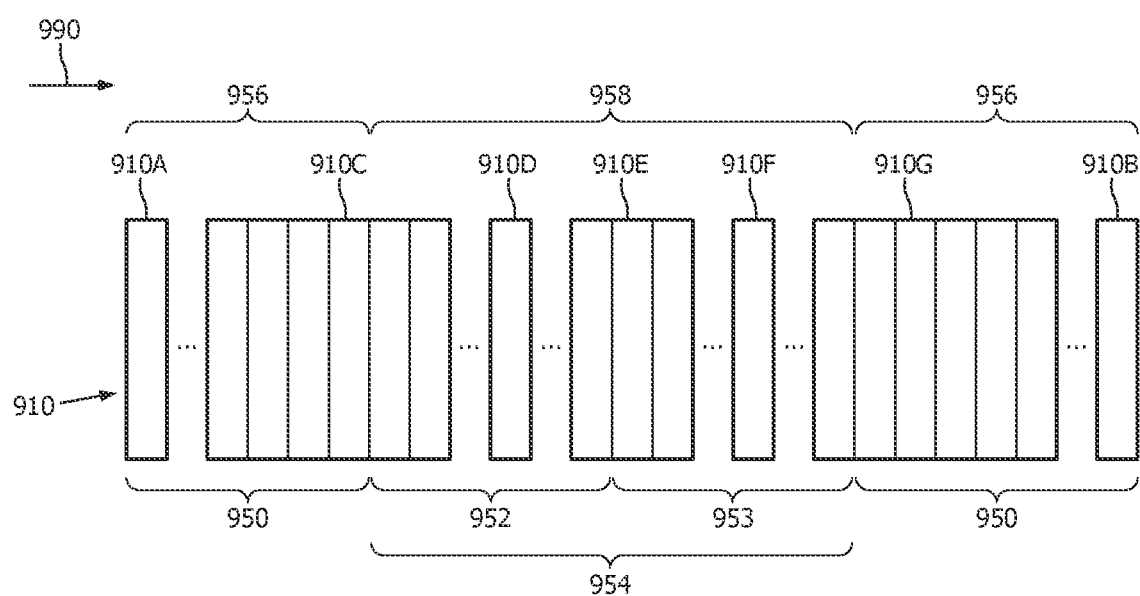
FIG. 9 is a schematic diagrammatic view of a series of intraluminal images received and analyzed by the intravascular imaging system, according to aspects of the present disclosure.

FIG. 9 is a schematic diagrammatic view of a series of intraluminal images received and analyzed by the intravascular imaging system, according to aspects of the present disclosure. FIG. 9 includes a graphical representation of a multiple intraluminal images 910 acquired by the intraluminal device 102 (FIG. 1) during an imaging procedure. The intraluminal images 910 may be intraluminal images acquired after the system has identified a location along the imaged vessel, the catheter is stationary, and the patient performs multiple deep breathing cycles. For example, referring to FIG. 4 and FIG. 6, the intraluminal images 910 may be acquired as the patient performs deep breathing cycles in response to the guidance of step 425 or step 625.

The arrow 990 indicates that the intraluminal images 910 displayed are ordered chronologically. For example, the intraluminal image 910A may be the first of the intraluminal images 910 in FIG. 9 obtained. The intraluminal image 910B may be the final of the intraluminal image 910 in FIG. 9 obtained. The indicators 950 identify intraluminal image 910 obtained while the patient was breathing normally. Indicators 956 identify intraluminal images 910 which were obtained while the catheter was moving. By contrast, the indicator 954 identifies intraluminal images 910 obtained while the patient as deep breathing. The indicator 958 identifies intraluminal images 910 obtained while the catheter was stationary. In the example shown in FIG. 9, therefore, the intraluminal images 910 identified by the indicators 954 and 956 may have been obtained after the system had identified a location of a potential candidate reference or compression frame, the user had stopped movement of the catheter, and the patient had begun deep breathing. In the example shown in FIG. 9, the intraluminal image 910C is the first intraluminal image obtained after the catheter became stationary as shown by the indicator 954 and is also the first intraluminal image obtained after the patient began deep breathing. In such an example, the physician stopped movement of the catheter at the same time the patient began deep breathing. In many applications, the physician may stop movement of the catheter at a different time than when the patient begins deep breathing. Similarly, the last intraluminal image obtained while the catheter was stationary is also the last image obtained while the patient was deep breathing. Again, the physician may begin movement at a different time than when the patient stops deep breathing and resumes normal breathing. However, in the example shown in FIG. 9, the period over which the catheter is stationary correlates exactly with the period over which the patient was breathing deeply for pedagogical purposes only and may not reflect expected or actual implementations of the methods described.

As mentioned, the intraluminal image 910C represents the first intraluminal image received after the catheter was stationary and the patient began deep breathing. As an example, the intraluminal image 910C may correspond to the first intraluminal image acquired after the patient began a deep inhale. As the patient continues to inhale, subsequent images acquired after image 910C may show the lumen progressively contracting until the inhale is complete and the patient begins a deep exhale. The intraluminal image 910D may be the image acquired when the patient stopped inhaling and started exhaling. As a result, as shown in FIGS. 10B and 11B hereafter, the image 910D may show the lumen in a state of minimum cross-sectional area. Whether the difference in cross-sectional area between the image 910C and 910D would depend largely on whether the location the catheter is positioned is a healthy region of the vessel or a compressed region of the vessel.

As the patient continues to exhale, the observed lumen may progressively expand again until the deep exhalation has been completed and the lumen has returned to its original size. The intraluminal image 910E may illustrate the vessel at this point in time after a complete exhalation has finished and an inhalation is begun. At this point, the vessel has again expanded to its original size. At this time, the vessel is likely at or near its maximum cross-sectional area. Depending on the consistency of the patient's deep breaths, the cross-sectional shape of the lumen as shown in the image 910E may be quite similar to the shape of the image 910C.

The system may compare each newly acquired intraluminal image 910 with the first intraluminal image 910C after the patient began deep breathing. In this way, it may determine when a complete deep breathing cycle has been completed. For example, the system may recognize that the shape of the lumen in image 910E is similar to the shape of the lumen in the image 910C and determine that the intraluminal images including 910C and the last image obtained before the image 910E form a single deep breathing cycle. That deep breathing cycle is identified by the indicator 952. The system may employ any of the methods previously described to compare the shapes of the lumen shown in the intraluminal images 910. For example, a threshold may be determined based on the two diameters of different axes as previously described, the cross-sectional area, or other measurements. When the change in shape between a newly acquired intraluminal image 910 and the first intraluminal image 910C of the deep breathing period is less than predetermined threshold, the system may determine that the newly acquired intraluminal image 910 is sufficiently similar to the image 910C and is designated as the start of a new deep breathing cycle 910E. Referring to FIG. 4, this criteria may trigger a "yes" response to the step 435 of the method 400. The same criteria may trigger a "yes" response to the step 635 of the method 600 of FIG. 6.

Displayed as acquired directly after this first deep breathing cycle 952, a second deep breathing cycle is shown by the indicator 953. In this second deep breathing cycle, the intraluminal image 910E may be the first image acquired during the second deep breathing cycle and may show the lumen at its maximum cross-sectional area. Similar to the first deep learning cycle 952, the lumen may then progressively contract following this first image 910E until the inhalation is complete and the patient begins to exhale at the time of the image 910F. The image 910F may then show the vessel at a minimum cross-sectional area. Just as the image 910E may be of a similar appearance as the image 910C, the image 910F may be of a similar appearance as the image 910D. As the patient exhales following the acquisition of the image 910F, the vessel may progressively expand to its maximum cross-sectional area at the time at which the image 910G is acquired.

Following 910G, the subsequent intraluminal images may have been obtained while the catheter was moving as shown by the indicator 950 and while the patient was breathing normally as shown by the indicator 956. In this example, the physician may have begun moving the catheter again and the patient may have begun normal breathing again in response to an output from the system of step 515 of the method 500 (FIG. 5) or step 715 of the method 700 (FIG. 7).

FIGS. 10A and 10B and FIGS. 11A and 11B illustrate exemplary cross-sectional shapes of a vessel as it is imaged while the catheter is held stationary and the patient breathes deeply.

Figure 10A:
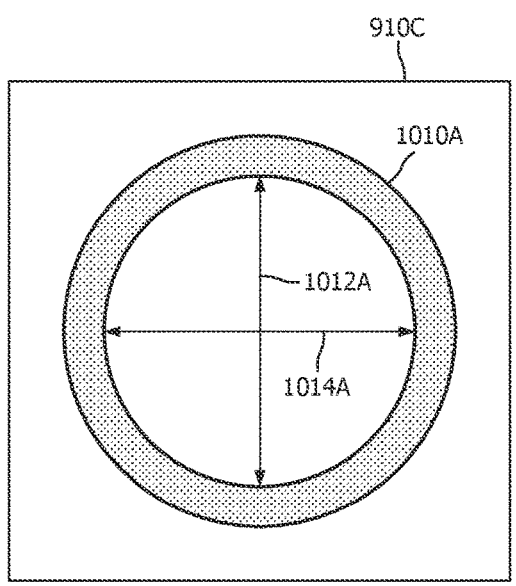
FIG. 10A is a diagrammatic view of an intraluminal image of a healthy section of a vessel obtained at the beginning of a deep breathing cycle, according to aspects of the present disclosure.
Figure 10B:
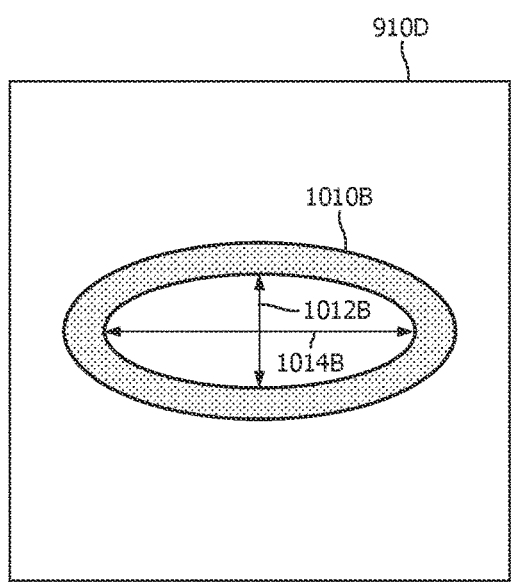
FIG. 10B is a diagrammatic view of an intraluminal image of a healthy section of a vessel obtained at a midpoint of a deep breathing cycle, according to aspects of the present disclosure.

FIG. 10A is a diagrammatic view of an intraluminal image of a healthy section of a vessel obtained at the beginning of a deep breathing cycle, according to aspects of the present disclosure. FIG. 10A will be described in conjunction with FIG. 10B which is a diagrammatic view of an intraluminal image of a healthy section of a vessel obtained at a midpoint of a deep breathing cycle, according to aspects of the present disclosure.

Referring back to FIG. 9, FIG. 10A shows an exemplary depiction of the intraluminal image 910C as the first intraluminal image obtained after the catheter is stationary as shown by the indicator 954 and the patient has begun deep breathing as shown by the indicator 958. For example, the intraluminal image 910C may be an image acquired after the patient has exhaled completely and begins to inhale deeply. Referring again to FIG. 10A, the vessel wall 1010A shows a cross-sectional shape of maximal size. A first diameter 1012A may be determined by the system along one axis drawn vertically across the lumen shape. A second diameter 1014A may also be determined by the system along a second axis drawn horizontally across the lumen shape. The diameters 1012A and 1014A may be used to measure the cross-sectional area of the lumen within the image 910C and/or to quantify the shape of the lumen of the image 910C. After exhalation, the vessel is at a maximum expansion. As a result, the diameters 1012A and 1014A may also be at a maximum.

FIG. 10B shows the image 910D (FIG. 9) depicting the same vessel at the same location at which the image 910C was acquired. However, the image 910D shows a view of the vessel after a deep, complete inhalation has occurred. As the patient finishes such an inhalation and begins to exhale, the vessel is at a minimum cross-sectional area as shown by FIG. 10B. The same diameters may be measured in a vertical and horizontal direction. For example, the diameter 1012B may indicate the diameter of the vessel along the same first vertical axis and the diameter 1014B may indicate the diameter of the vessel along the second horizontal axis. As shown in FIGS. 10A and 10B, the diameter 1014B (FIG. 10B) may be largely unchanged from the diameter 1014A (FIG. 10A). However, the diameter 1012B (FIG. 10B) may be significantly less than the diameter 1012A (FIG. 10A) accounting for a great change in cross-sectional area of the lumen at the time at which the image 910D was acquired.

Referring back to step 505 of method 500 (FIG. 5), such an observed change in the lumen shape of an imaged vessel may return a "yes" response to the step 505 if the change exceeds the threshold change required. As a result, at step 510, the image 910C may be selected as a candidate reference frame if it does in fact show the maximum cross-sectional area of the lumen observed throughout the deep breathing cycle.

Figure 11A:
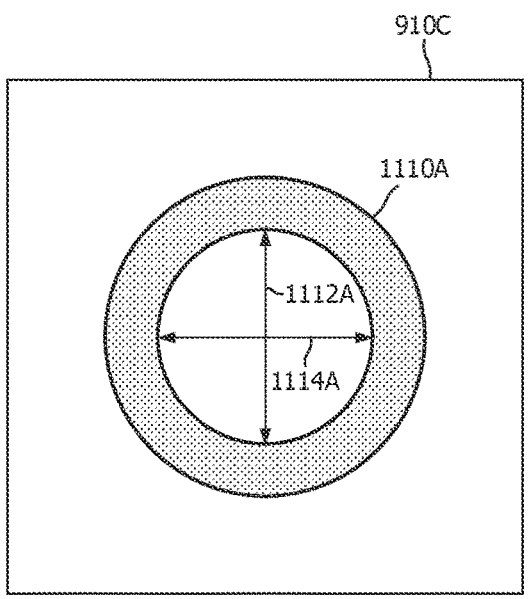
FIG. 11A is a diagrammatic view of an intraluminal image of a constricted section of a vessel obtained at the beginning of a deep breathing cycle, according to aspects of the present disclosure.
Figure 11B:
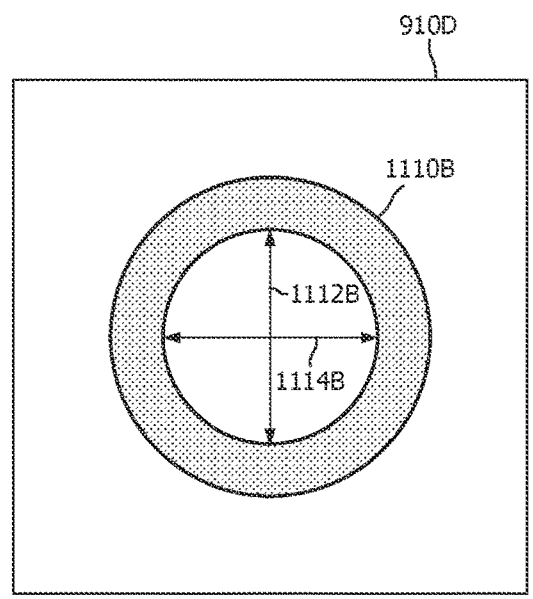
FIG. 11B is a diagrammatic view of an intraluminal image of a constricted section of a vessel obtained at a midpoint of a deep breathing cycle, according to aspects of the present disclosure.

FIG. 11A is a diagrammatic view of an intraluminal image of a constricted section of a vessel obtained at the beginning of a deep breathing cycle, according to aspects of the present disclosure. FIG. 11A will be described in conjunction with FIG. 11B which is a diagrammatic view of an intraluminal image of a constricted section of a vessel obtained at a midpoint of a deep breathing cycle, according to aspects of the present disclosure.

Referring back to FIG. 9, FIG. 11A shows an alternate exemplary depiction of the intraluminal image 910C if the region imaged was a constricted or compressed region such as the region 304 of FIG. 3. The intraluminal image 910C shown in FIG. 11A may be an image acquired after the patient has exhaled completely and begins to inhale deeply. Referring again to FIG. 11A, the vessel wall 1110A shows a cross-sectional shape of maximal size. A first diameter 1112A may be determined by the system along the vertical axis and a second diameter 1114A may be determined along the horizontal axis. Like the diameters 1012A and 1014A, the diameters 1112A and 1114A may be used to measure the cross-sectional area of the lumen within the image 910C and/or to quantify the shape of the lumen. Similar to FIG. 10A, after exhalation, the vessel is at a maximum expansion. As a result, the diameters 1112A and 1114A may also be at a maximum.

FIG. 10B shows an alternate version of the image 910D (FIG. 9) if the imaged region was a compressed region. FIG. 11B depicts the same vessel at the same location at which the image 910C of FIG. 11A was acquired. However, the image 910D of FIG. 11B shows a view of the vessel after a deep, complete inhalation has occurred. As the patient finishes such an inhalation and begins to exhale, the vessel is at a minimum cross-sectional area. However, because the region imaged in FIGS. 11A and 11B is a constricted region, there is little or no change to the cross-sectional area or shape of the vessel between the image showing maximum expansion and maximum compression in FIGS. 11A and 11B respectively. In the image 910D of FIG. 11B, the diameters 1112B and 1114B may be measured in a vertical and horizontal direction. As shown in FIGS. 11A and 11B, the diameters 1112B and 1114B (FIG. 11B) are both largely unchanged from the diameters 1012A and 1014A (FIG. 10A).

Referring back to step 705 of method 700 (FIG. 7), such an observed lack of change in the lumen shape of an imaged vessel may return a "yes" response to the step 705 if the change remains below the threshold change required. As a result, at step 710, the image showing the greatest cross-sectional area may be selected as a candidate compression frame.

Figure 12:
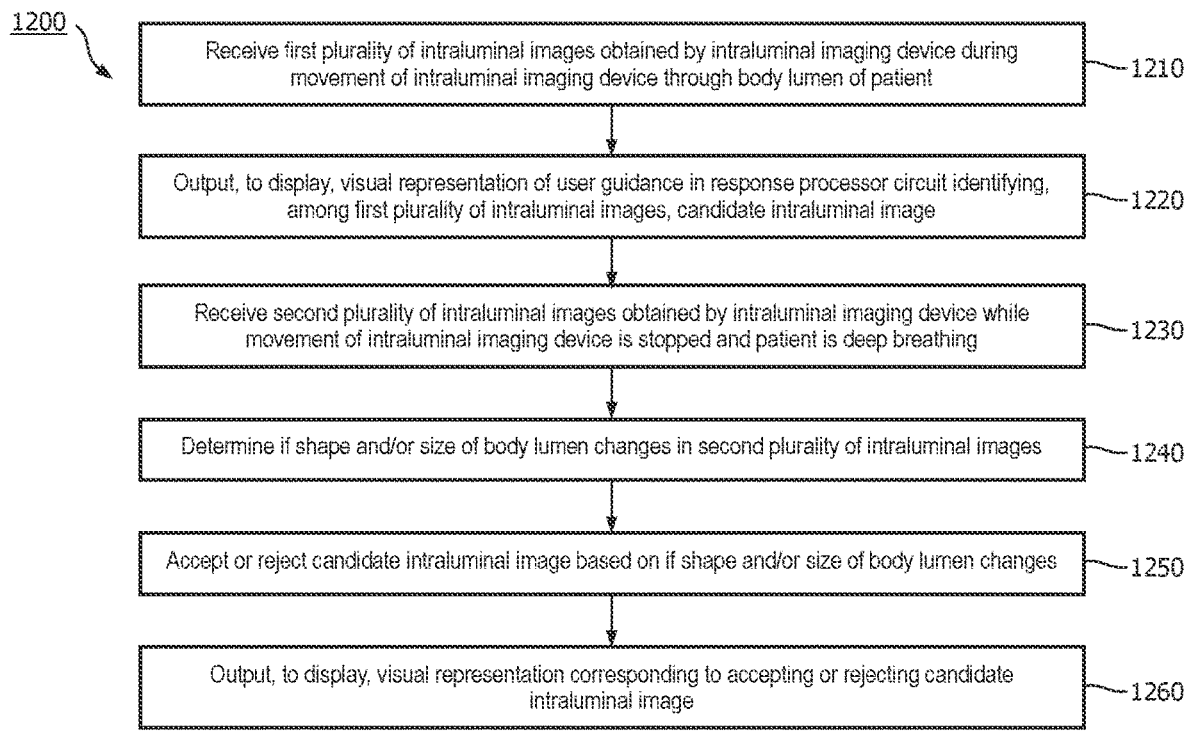
FIG. 12 is a flow diagram for a method of identifying candidate reference and compression frames, according to aspects of the present disclosure.

FIG. 12 is a flow diagram for an intraluminal imaging method, according to aspects of the present disclosure. As illustrated, the method 1200 includes a number of enumerated steps, but embodiments of the method 1200 may include additional steps before, after, or in between the enumerated steps. In some embodiments, one or more of the enumerated steps may be omitted, performed in a different order, or performed concurrently. The steps of the method 1200 can be carried out by any suitable component within the system 100 and all steps need not be carried out by the same component. In some embodiments, one or more steps of the methods 1200 can be performed by, or at the direction of, a processor circuit of the system 100 (e.g., the processor circuit 210 of FIG. 2), including, e.g., the processor 260 or any other component.

At step 1210, the method 1200 includes receiving a first plurality of intraluminal images obtained by the intraluminal imaging device during movement of the intraluminal imaging device through a body lumen of a patient. For example, the processor circuit can receive a first plurality of IVUS images obtained by the IVUS imaging catheter during movement of the IVUS imaging catheter through a peripheral vein of a patient.

At step 1220, the method 1200 includes outputting, to a display, a visual representation of first user guidance in response the processor circuit identifying, among the first plurality of intraluminal images, a candidate intraluminal image. The first user guidance includes stopping the movement of the intraluminal imaging device and/or instructing the patient to initiate deep breathing. For example, the processor circuit can output, to the display, a visual representation of user guidance in response the processor circuit identifying, among the first plurality of IVUS images, a candidate IVUS image. The user guidance includes stopping the movement of the IVUS imaging catheter and/or instructing the patient to initiate deep breathing;

At step 1230, the method 1200 includes receiving a second plurality of intraluminal images obtained by the intraluminal imaging device while the movement of the intraluminal imaging device is stopped and the patient is deep breathing. For example, the processor circuit can receive a second plurality of IVUS images obtained by the IVUS imaging catheter while the movement of the IVUS imaging catheter is stopped and the patient is deep breathing.

At step 1240, the method 1200 includes determining if a shape of the body lumen changes in the second plurality of intraluminal images. For example, the processor circuit can determine if a shape of the peripheral vein changes in the second plurality of IVUS images.

At step 1240, the method 1200 includes accepting or rejecting the candidate intraluminal image based on if the shape of the body lumen changes. For example, the processor circuit can accept or reject the candidate intraluminal image as a reference IVUS image or a compression IVUS image based on if the shape of the peripheral vein changes.

At step 1250, the method 1200 includes outputting, to the display, a visual representation corresponding to accepting or rejecting the candidate intraluminal image. For example, the processor circuit can output, to the display, a visual representation corresponding to accepting or rejecting the candidate IVUS image. The output can be user guidance to resume movement of intraluminal imaging device. The output can be user guidance to instruct the patient to stop deep breathing and/or resume ordinary breathing. The output can be a visual representation that the candidate intraluminal image has been accepted (e.g., green border around intraluminal image, check mark on screen display, etc.) or rejected (e.g., red border, around intraluminal image, prohibition or circle-backslash symbol on screen display). In some instances, the output can be audible (e.g., correct sound effect/ding, incorrect sound effect/buzzer, etc.). Referring again to step 1230 of the method 1200, the system 100 may automatically generate a bookmark (e.g., an autobookmark) indicating a frame as a target or reference frame after the second plurality of intraluminal images is obtained. At the step 1260, the system 100 may generate feedback including an indication to remove the autobookmark created at or after step 1230. In some embodiments, the feedback may include an indication to confirm the autobookmark. In some embodiments, the system 100 may automatically remove or confirm an autobookmark.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
an intravascular imaging catheter; and
a processor circuit configured for communication with the intravascular imaging catheter and a display, wherein the processor circuit is configured to:
control the intravascular imaging catheter to obtain a first plurality of intravascular images during a pullback of the intravascular imaging catheter through a blood vessel comprising a region of constricted blood flow, wherein the region comprises a target location and a reference location;
identify, from among the first plurality of intravascular images, a first intravascular image obtained at a first location as a candidate to represent one of the target location or the reference location;
output, to the display, a graphical user interface (GUI) for planning a treatment for the constricted blood flow comprising a stent positioned at the target location and the reference location, wherein the GUI comprises a visual representation of first user guidance, wherein the first user guidance comprises stopping the pullback of the intravascular imaging catheter at the first location and instructing the patient to initiate deep breathing;
control the intravascular imaging catheter to obtain a second plurality of intravascular images while the pullback of the intravascular imaging catheter is stopped at the first location and the patient is deep breathing;
determine, in the second plurality of intravascular images, if at least one of a shape or a size of the blood vessel changes at the first location;
accept or reject the first intravascular image as representing the target location or the reference location based on if at least one of the shape or the size of the blood vessel changes at the first location; and
output, via the GUI on the display, a visual representation corresponding to accepting or rejecting the first intravascular image as the representing the target location or the reference location.

2. The system of claim 1, wherein the processor circuit is configured to reject the first intravascular image as representing the reference location in response to at least one of the shape or the size of the blood vessel not changing in the second plurality of intravascular images.

3. The system of claim 1, wherein the processor circuit is configured to accept the first intravascular image as representing the reference location in response to at least one of the shape or the size of the blood vessel changing in the second plurality of intravascular images.

4. The system of claim 1, wherein the processor circuit is configured to select, from the second plurality of intravascular images, a second intravascular image with a largest lumen as a reference intravascular image for the reference location.

5. The system of claim 4,
wherein the processor circuit is configured to output, via the GUI on the display, a visual representation of second user guidance,
wherein the second user guidance comprises resuming the pullback of the intravascular imaging catheter and instructing the patient to stop deep breathing.

6. The system of claim 1, wherein the processor circuit is configured to reject the first intravascular image as representing the target location in response to at least one of the shape or the size of the blood vessel changing in the second plurality of intravascular images.

7. The system of claim 1, wherein the processor circuit is configured to accept the first intravascular image as representing the target location in response to at least one of the shape or the size of the blood vessel not changing in the second plurality of intravascular images.

8. The system of claim 1, wherein the processor circuit is configured to select, from the second plurality of intravascular images, a second intravascular image with a largest lumen as a target intravascular image for the target location.

9. The system of claim 8, wherein the processor circuit is configured to output, via the GUI on the display, a visual representation of second user guidance, wherein the second user guidance comprises resuming the pullback of the intravascular imaging catheter and instructing the patient to stop deep breathing.

10. The system of claim 1, wherein the processor circuit is configured to determine if the pullback of the intravascular imaging catheter is stopped.

11. The system of claim 1, wherein the processor circuit is configured to determine whether the second plurality of intravascular images comprises a complete deep breathing cycle.

12. The system of claim 1, wherein the processor circuit is configured to determine if at least one of the shape or the size of the blood vessel changes based on an aspect ratio of the blood vessel in the second plurality of intravascular images.

13. The system of claim 1, wherein the blood vessel comprises a peripheral vein.

14. The system of claim 1, wherein the intravascular imaging catheter comprises an intravascular ultrasound (IVUS) catheter or an optical coherence tomography (OCT) catheter.

* * * * *